United States Patent
Hsieh

(10) Patent No.: US 6,647,084 B1
(45) Date of Patent: Nov. 11, 2003

(54) METHOD AND APPARATUS FOR FILTERING PROJECTION DATA OF A HELICAL SCAN

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/065,692

(22) Filed: Nov. 11, 2002

(51) Int. Cl.[7] ................................................ A61B 6/03
(52) U.S. Cl. ................................ 378/4; 378/15; 378/94
(58) Field of Search ............................ 378/4, 8, 15, 94

(56) References Cited

U.S. PATENT DOCUMENTS

| | | | |
|---|---|---|---|
| 5,170,439 A | * 12/1992 | Zeng et al. | 382/131 |
| 5,430,783 A | 7/1995 | Hu et al. | 378/15 |
| 5,963,614 A | 10/1999 | Hu et al. | 378/15 |
| 6,108,575 A | 8/2000 | Besson | 600/425 |
| 6,292,526 B1 | 9/2001 | Patch | 378/4 |
| 6,332,013 B1 | 12/2001 | Hsieh | 378/15 |
| 6,408,042 B1 | * 6/2002 | Hsieh | 378/4 |

* cited by examiner

Primary Examiner—David V. Bruce
(74) Attorney, Agent, or Firm—Cantor Colburn LLP

(57) ABSTRACT

A method for filtering projection data of a helical scan of an object includes acquiring projection data representing a helical scan of an object, generating a weighting function based on the acquired projection data, determining a scaling function for the weighting function, and determining a row-filtered weighting function based on the weighting function and scaling function.

22 Claims, 4 Drawing Sheets

METHOD AND APPARATUS FOR FILTERING PROJECTION DATA OF A HELICAL SCAN

BACKGROUND OF THE INVENTION

This invention relates generally to a tomographic scanning system, and more particularly to a method and apparatus for filtering projection data of a helical scan.

Helical computed tomography (CT) has become the method of choice for many routine clinical studies, which requires the application of a helical reconstruction algorithm for the reconstruction of a projection image from the projection data. In at least one known helical scanning system using a CT, an x-ray source and a detector array rotate with a gantry within the imaging plane and around the object to be imaged, such as a patient, while the patient is moved through the gantry in a direction perpendicular to the imaging plane, resulting in a constantly changing angle and location at which the x-ray beam intersects the scanned object. The x-ray fan beam passing through the object is attenuated before it impinges upon the array of radiation detectors. In response, the radiation detectors each produce a signal having a magnitude dependent on the intensity of the attenuated beam. The attenuation measurements from all the detectors over the duration of the helical scan are acquired to produce a scan profile, or set of projection data. The set of projection data resulting from the helix mapped out by the fan beam can be analyzed to reconstruct images of the scanned object.

One method of reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display. Reconstruction algorithms for helical scanning typically use weighting functions that weight the collected data as a function of the detector angle and projection angle, and where multiple rows of detectors are used, as a function of row position also. Filtering methods to reduce noise and suppress artifacts are applied to the projection data, thereby producing an overall improvement in quality image. However, some filtering methods, such as z-filtering, requires filtering in the projection-angle-direction, which requires an increase in the number of views and an increase in scan time.

BRIEF DESCRIPTION OF THE INVENTION

In one embodiment, a method for filtering projection data of a helical scan of an object includes acquiring projection data representing a helical scan of an object, generating a weighting function based on the acquired projection data, determining a scaling function for the weighting function and determining a row-filtered weighting function based on the weighting function and scaling function.

In another embodiment, a system for producing a scanned image of an object includes a computer programmed to acquire projection data representative of a helical scan of an object, generate a weighting function based on the acquired projection data, determine a scaling function for the weighting function, and determine a row-filtered weighting function based on the weighting function and scaling function.

BRIEF DESCRIPTION OF THE DRAWINGS

Referring now to the figures, which are exemplary embodiments, and wherein like elements are numbered alike.

Detailed Description

A detailed description of an embodiment of the present invention is presented herein by way of exemplification and not limitation with reference to FIGS. 1–11.

Figure 1:
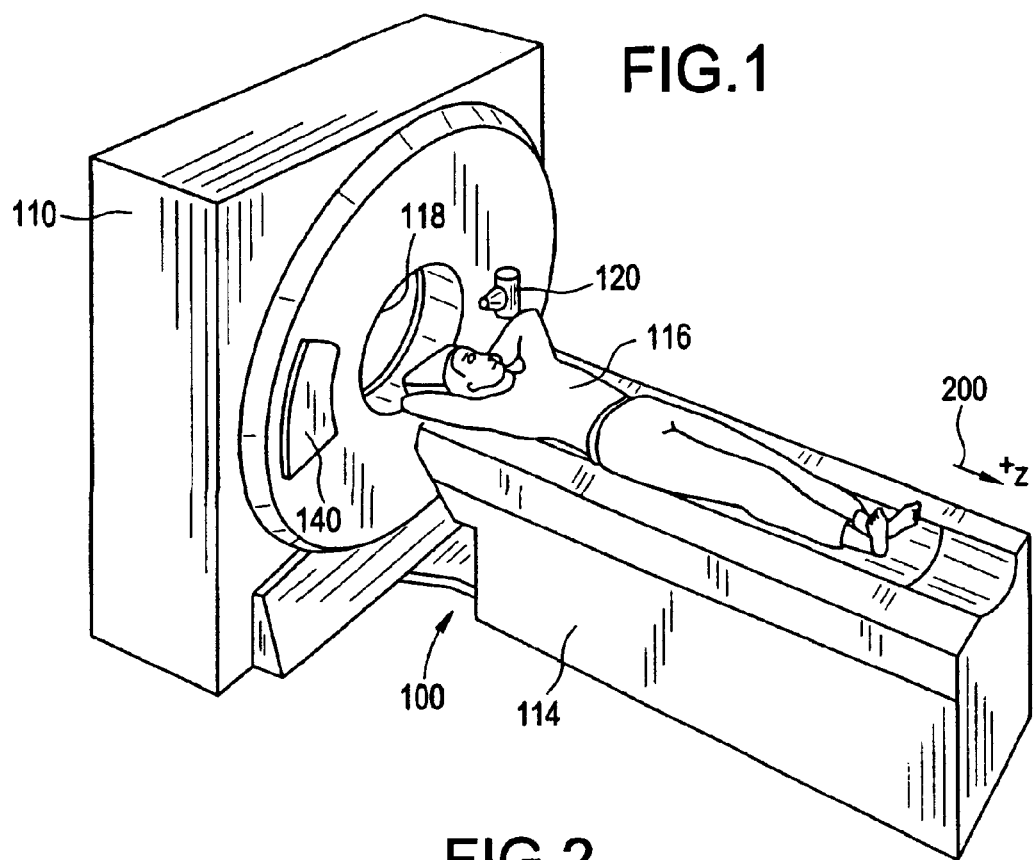
FIG. 1 depicts a generalized pictorial view of a CT imaging system for use in accordance with an embodiment of the invention.
Figure 2:
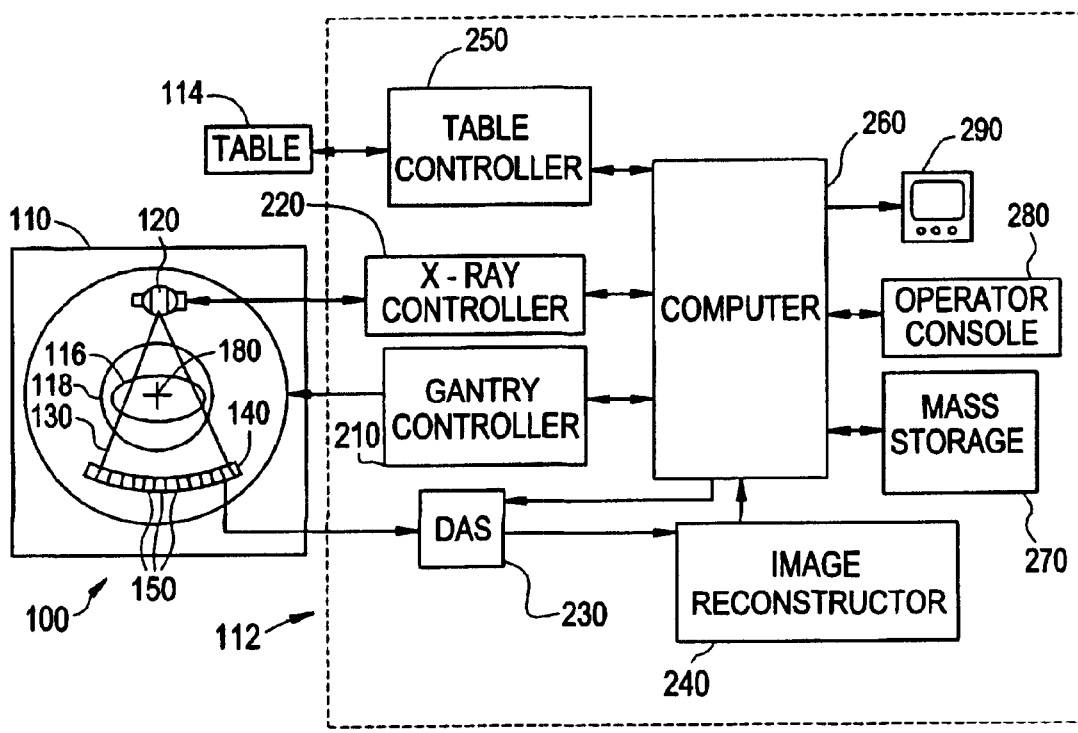
FIG. 2 depicts a generalized block schematic diagram of the imaging system of FIG. 1.

Referring to FIGS. 1 and 2, a computed tomograph (CT) imaging system 100 is shown having a gantry 110, which is representative of a CT scanner, a control system 112, and a motorized table 114 for positioning an object 116, such as a patient, in gantry opening 118 in gantry 110. Gantry 110 includes an x-ray source that projects a fan beam of x-rays 130 toward a detector array 140 on the opposite side of gantry 110. Detector array 140 is formed by detector elements 150, which are shown in more detail in FIG. 3 and discussed below. Detector elements 150 are radiation detectors that each produces a signal having a magnitude that represents and is dependent on the intensity of the attenuated x-ray beam after it has passed through patient 116 being imaged. During a helical scan that acquires x-ray projection data, the gantry 110 along with the x-ray source 120 and detector array 140 rotate within the imaging plane and around the patient 116 about a center of rotation 180, while the patient 116 is moved through the gantry in a z-direction 200 perpendicular to the imaging plane.

Gantry 110 and x-ray source 120 are controlled by control system 112, which includes a gantry controller 210, an x-ray controller 210, a data acquisition system (DAS) 220, an image reconstructor 240, a table controller 250, a computer 260, a mass storage-system 270, an operator interface 280, and a display device 290. Gantry controller 210 controls the rotational speed and position of gantry 110, x-ray controller 220 provides power and timing signals to x-ray source 120, data acquisition system 220 acquires analog data from detector elements 150 and converts the data to digital form for subsequent processing, image reconstructor 240 receives the digitized x-ray data from DAS 230 and performs an image reconstruction process that involves filtering the projection data by using a helical reconstruction algorithm discussed in detail below, and table controller 250 controls motorized table 114 to position patient 116 in gantry opening 118.

Computer 260 is in operable communication with gantry controller 210, x-ray controller 220, and table controller 250 whereby control signals are sent from the computer to controllers 210, 220, 250 and information is received from the controllers by computer 260. Computer 260 also provides commands and operational parameters to DAS 230 and receives reconstructed image data from image reconstructor 240. The reconstructed image data is stored by computer 260 in a mass storage device 270 for subsequent retrieval. An operator interfaces with computer 260 through operator interface 280, which may include, for example, a keyboard and a graphical pointing device, and receives output, such as, for example, a reconstructed image, control settings and other information, on a display device 290.

Operable communication between the various system elements of FIG. 1 is depicted by arrowhead lines, which illustrate a means for either signal communication or mechanical operation, depending on the system element involved. Operable communication amongst and between the various system elements may be obtained through a hardwired or a wireless arrangement. Computer 260 may be a standalone computer or a network computer and may include instructions in a variety of computer languages for use on a variety of computer platforms, such as, for example, DOS-based systems, Apple-based systems, Windows-based systems, HTML-based systems, or the like.

Figure 3:
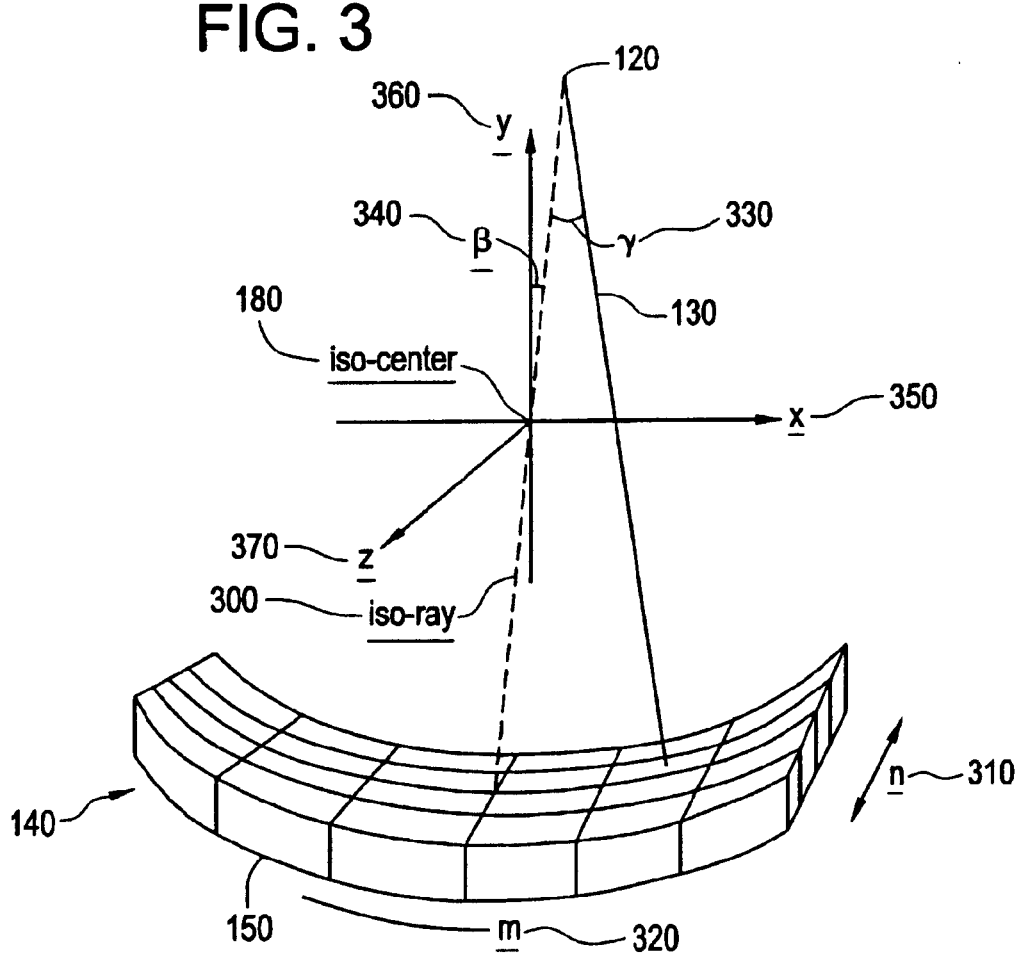
FIG. 3 depicts a diagram showing the coordinates used in the imaging system of FIG. 1.

Referring now to FIG. 3, an illustration of x-ray beam 130, having a beam axis (iso-ray) 300 that originates at x-ray source 120 and passes through center of rotation (iso-center) 180, relative to detector array 140, having detector elements 150 arranged in rows n 310 and columns m 320, is provided. While FIG. 3 depicts only four rows 310 (n=4) and six columns 320 (m=6), it will be appreciated that any number of rows and columns may be employed as a matter of design choice. In an embodiment of the present invention, n=16 and m=900. The parameters n and m are alternatively referred to herein as detector row n and detector column m, respectively. As depicted in FIG. 3, a detector angle γ 330 is shown as an angle formed between detector cell m and the iso-ray 300 which connects the x-ray source 120 and the iso-center 180, and a projection angle β 340 is shown as an angle formed by the iso-ray 300 with the y-axis 360.

An embodiment of the present invention employs a row-filtered projection reconstruction procedure. Certain projection reconstruction techniques, such as, for example, z-filtered projection reconstruction, are known in the art, however, row-filtered projection reconstruction is performed in accordance with an embodiment of the invention and involves the filtering of the projection data from the helical scan of the patient 116 using a row-filtering weighting function. A flowchart for implementing the row-filtered projection reconstruction process in accordance with an embodiment of the invention is depicted in FIG. 4.

Figure 4:
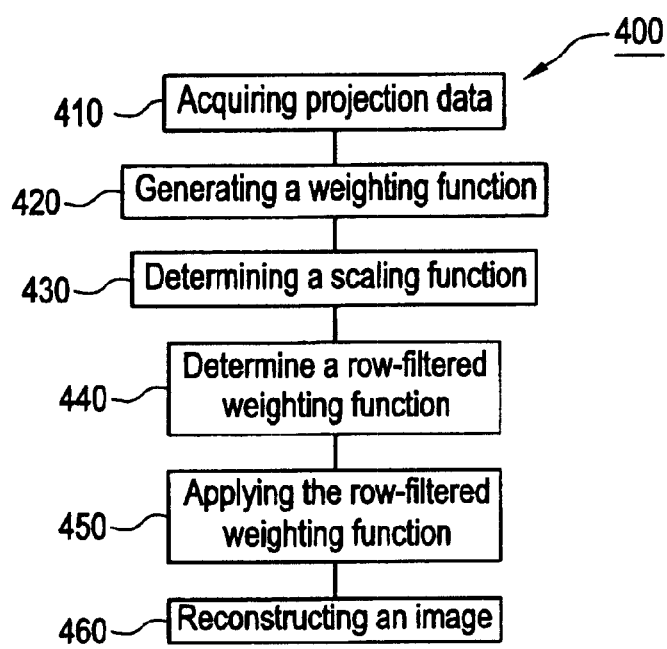
FIG. 4 depicts a process flowchart for implementing the image reconstruction method in accordance with an embodiment of the invention.
Figure 5:
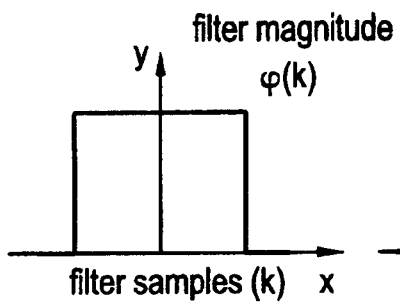
FIGS. 5–9 depict graphical representations of scaling functions for use in accordance with an embodiment of the invention.
Figure 6:
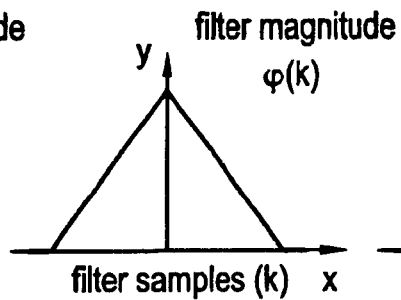
Figure 7:
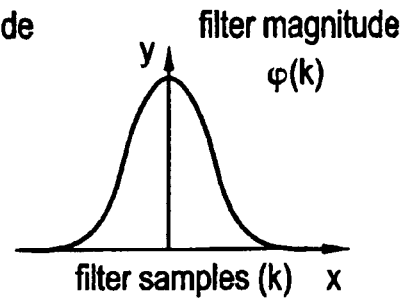
Figure 8:
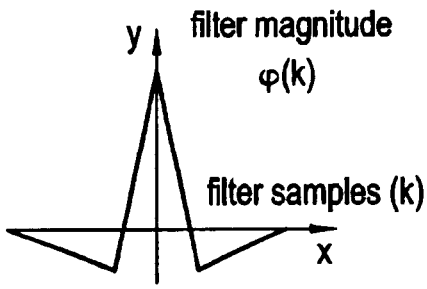
Figure 9:
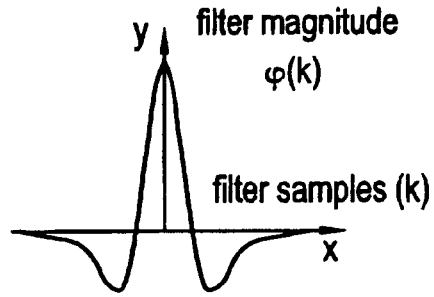

In FIG. 4, process 400 begins with the acquisition 410 of projection data representative of the helical scan of patient 116, where the measured projection data is denoted by p(γ, β,n). From the measured projection data, a reconstructed image is produced, denoted by l(x,y). To produce the reconstructed image l(x,y), a weighting function based on the acquired projection data is employed, denoted by w(γ, β,n), which is generated at step 420 using a helical interpolation weighting function algorithm employed by the software in image reconstructor 240. Next, at step 430, a scaling function is determined, denoted by φ(k), which can be either a low-pass (row-smoothing), a high-pass (row sharpening), or another type of filter. FIGS. 5–7 depict examples of box-car, triangular and Gaussian low-pass filters, respectively, and FIGS. 8–9 depict examples of high-pass filters. While FIGS. 5–9 depict specific examples of low and high-pass filters, it will be appreciated that there is an unlimited number of filters that may be employed for the scaling function, and the present invention is not limited to the selection of a particular filter. The value of k ranges from −K to +K, and by adjusting φ(k) and the size of K, different slice sensitivity profiles (SSP), smooth or sharp, may be obtained. At step 440, a row-filtered weighting function w'(γ, β,n) is determined in accordance with Equation-1

$$w'(\gamma, \beta, n) = \sum_{k=-K}^{K} [\varphi(k) w(\gamma, \beta, n+k)] \quad \text{Equa. 1}$$

Equation-1 is a discrete form of an equivalent integral equation, and is used for computational purposes. Note that the filtering of the boundary samples (for n<k and n>N−k), where N is the number of detector rows, Equation 1 cannot be applied directly. Under these conditions, several methods can be used. One such method is to replicate the boundary samples so that the original projection is artificially expanded to N+2k rows. That is, the original projection, p(γ, β,n), becomes {p(γ, β,0), . . . , p(γ, β,0), p(γ, β,1), p(γ, β,2), . . . , p(γ, β,N), p(γ, β,N), . . . , p(γ, β,N)}. Alternatively, special scaling function φ(k) can be derived for the boundary samples to match the number of available samples.

At step 450, the row-filtered weighting function w'(γ, β,n), which now includes row-smoothed or row-sharpened data, depending on the scaling function φ(k) employed, is applied to the projection data p(γ, β,n) to produce the final weighted projection dataset.

At step 460, the weighted projection dataset is then filtered and backprojected (using known method called filtered backprojection) to produce the reconstructed image l(x,y). Alternatively, the original projection data p(γ, β,n) is filtered by the scaling function φ(k) to produce a new set of projections, p'(γ, β,n). The helical weighting function w(γ, β,n) is then applied to the new projection to produce reconstructed images. At step 460, the image l(x,y) is reconstructed using a filtered backprojection reconstruction algorithm employed by the software in image reconstructor 240. In accordance with an embodiment of the invention, the resulting reconstructed image is a helical image reconstruction with row-filtration.

Figure 10:
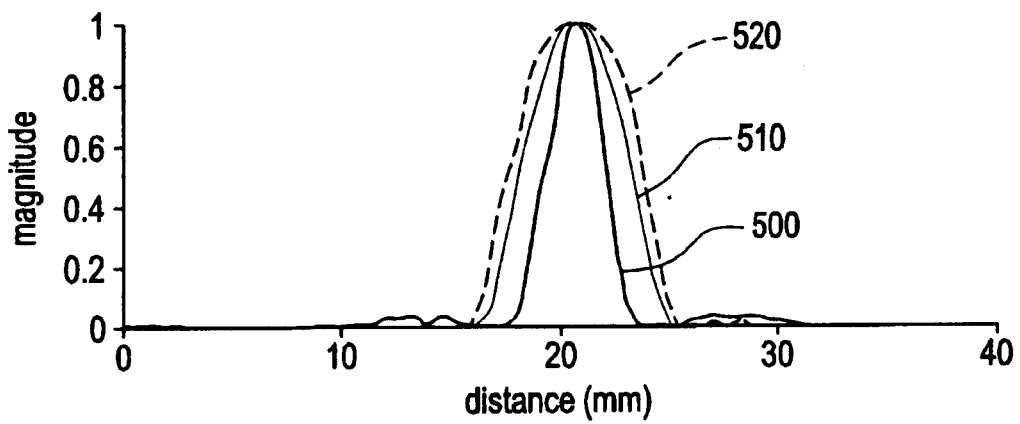
FIG. 10 depicts graphical representations of a scanned thin disc phantom with an embodiment of the invention shown comparatively.
Figure 11:
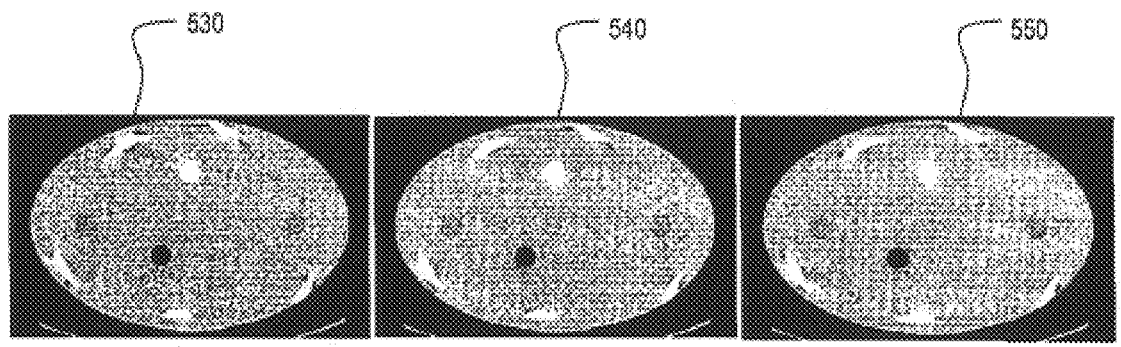
FIG. 11 depicts graphical representations of a scanned helical body phantom with an embodiment of the invention shown comparatively.

Referring now to FIGS. 10 and 11, scanned data from a thin disc phantom and a helical body phantom are presented, respectively. The thin disc phantom is primarily used to measure the SSP of the resulting reconstruction, while the helical body phantom is primarily used to indicate the artifact suppression level. FIG. 10 depicts the reconstructed SSP for the native mode (no filtering) 500, the z-filtering operation 510, and the row-filtering operation 520. As shown in FIG. 10, the full width half magnitudes (FWHMs) for the z-filtering and row-filtering operations are comparable in value. FIG. 11 depicts the image artifacts suppression for the native mode (no filtering) 530, the z-filtering operation 540, and the row-filtering operation 550. As shown in FIG. 11, the images produced by the z-filtering and row-filtering operations are comparable in image quality.

As shown by FIGS. 10 and 11, the row-filtering operation produces a reconstructed image that is comparable in quality to the reconstructed image from the z-filtering operation. However, since the row-filtering method does not filter the projection image data in the β-direction, as does the z-filtering method, fewer views are needed for image reconstruction, thereby reducing the amount of scan time required. As a result, the row-filtering method produces a reconstructed image having a greater temporal resolution as compared to a reconstructed image from the z-filtering method. Since the row-filtering method results in less scan time, the benefits are two-fold: first, the patient is exposed to less radiation, and second, the data collection process is less time-sensitive, and therefore less sensitive to patient motion during scanning. An alternative way to consider the benefits of the present invention is to look at the number of projection views required for image reconstruction. Since the row-filtering method can produce a thicker image slice as compared to no filtering from the same number of views, a reduction in noise and artifacts can be achieved without a reduction in temporal resolution. And, since the row-filtering method can produce the same image quality as compared to the z-filtering method but in less time, an improvement in image reconstruction speed can be achieved in terms of both time-to-first-image and time-between-images, thereby improving the efficacy of the medical procedure.

In an alternative embodiment, a step-and-shoot mode of scanning can be used in place of helical scanning for providing projection data. In the step-and-shoot case, a scaling function is used for row-filtering and is applied to each projection prior to the filtered backprojection. Here, a weighting function (such as halfscan or underscan) can be used in combination with the step-and-shoot projection to reduce patient motion artifacts or to improve temporal resolution. The scaling function can be combined with these weighting functions in a similar manner as the helical scan case. Helical and step-and-shoot scanning are referred to collectively as tomographic scanning.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for filtering projection data of a tomographic scan of an object, comprising:

acquiring projection data representing a tomographic scan of an object;

generating a weighting function based on the acquired projection data;

determining a scaling function for the weighting function; and determining a row-filtered weighting function based on the weighting function and scaling function.

2. The method for filtering set forth in claim 1, further comprising:

applying the row-filtered weighting function to the projection data.

3. The method for filtering set forth in claim 1, wherein the tomographic scan of said acquiring projection data representing a tomographic scan comprises at least one of a helical scan or a step-and-shoot scan.

4. The method for filtering set forth in claim 1, wherein said generating a weighting function comprises:

generating a weighting function that is row-variant.

5. The method for filtering set forth in claim 4, wherein said determining a row-filtered weighting function further comprises:

determining a row-filtered weighting function according to the equation $$w'(\gamma, \beta, n) = \sum_{k=-K}^{K} [\varphi(k)w(\gamma, \beta, n+k)]$$

6. The method for filtering set forth in claim 5, further comprising:

producing a final weighted projection dataset by applying the row-filtered weighting function to the projection data; and reconstructing an image by filtering and backprojecting the weighted projection dataset.

7. The method for filtering set forth in claim 6, wherein said reconstructing an image further comprises:

reconstructing an image having a FWHM comparable to a reconstructed image from a z-filtering reconstruction method.

8. The method for filtering set forth in claim 7, wherein said reconstruction and image further comprises:

reconstructing an image having a reduced scan time as compared to a reconstructed image from a z-filtering reconstruction method.

9. The method for filtering set forth in claim 1, wherein said generating a weighting function comprises:

generating a weighting function based on a low-pass filter.

10. The method for filtering set forth in claim 1, wherein said generating a weighting function comprises:

generating a weighting function based on a high-pass filter.

11. The method for filtering set forth in claim 9, wherein said generating a weighting function further comprises:

generating a weighting function based on a low-pass filter selected from the group consisting of a box-car low-pass filter, a triangular low-pass filter, and a Gaussian low-pass filter.

12. A system for producing a scanned image of an object, said system comprising a computer programmed to:

acquire projection data representative of a tomographic scan of an object;

generate a weighting function based on the acquired projection data;

determine a scaling function for the weighting function; and determine a row-filtered weighting function based on the weighting function and scaling function.

13. The system of claim 12, wherein said system further comprises a computer programmed to:

apply the row-filtered weighting function to the projection data.

14. The system of claim 12, wherein said system further comprises a computer programmed to:

acquire projection data representative of at least one of a helical scan or a step-and-shoot scan of an object.

15. The system of claim 12, wherein said system further comprises a computer programmed to:

generate a weighting function that is row-variant.

16. The system of claim 15, wherein said system further comprises a computer programmed to:

determine a row-filtered weighting function according to the equation $$w'(\gamma, \beta, n) = \sum_{k=-K}^{K} [\varphi(k)w(\gamma, \beta, n+k)]$$

17. The system of claim 16, wherein said system further comprises a computer programmed to:
    produce a final weighted projection dataset by applying the row-filtered weighting function to the projection data; and
    reconstruct an image by filtering and backprojecting the weighted projection dataset.

18. The system of claim 17, wherein said system further comprises a computer programmed to:
    reconstruct an image having a FWHM comparable to a reconstructed image from a z-filtering reconstruction method.

19. The system of claim 18, wherein said system further comprises a computer programmed to:
    reconstruct an image having a reduced scan time as compared to a reconstructed image from a z-filtering reconstruction method.

20. The system of claim 12, wherein said system further comprises a computer programmed to:
    generate a weighting function based on a low-pass filter.

21. The system of claim 12, wherein said system further comprises a computer programmed to:
    generate a weighting function based on a high-pass filter.

22. The system of claim 20, wherein said system further comprises a computer programmed to:
    generate a weighting function based on a low-pass filter selected from the group consisting of a box-car low-pass filter, a triangular low-pass filter, and a Gaussian low-pass filter.

* * * * *